(12) United States Patent
Johnson

(10) Patent No.: US 10,568,485 B2
(45) Date of Patent: Feb. 25, 2020

(54) SHOE DISINFECTING ASSEMBLY

(71) Applicant: Marilou Johnson, Richmond, KY (US)

(72) Inventor: Marilou Johnson, Richmond, KY (US)

( * ) Notice: Subject to any disclaimer, the term of this patent is extended or adjusted under 35 U.S.C. 154(b) by 0 days.

(21) Appl. No.: 16/033,935

(22) Filed: Jul. 12, 2018

(65) Prior Publication Data

US 2020/0015650 A1    Jan. 16, 2020

(51) Int. Cl.
*A61L 2/18* (2006.01)
*A47L 13/17* (2006.01)

(52) U.S. Cl.
CPC .................. *A47L 13/17* (2013.01); *A61L 2/18* (2013.01)

(58) Field of Classification Search
CPC .................................... A47L 13/17; A61L 2/18
See application file for complete search history.

(56) References Cited

U.S. PATENT DOCUMENTS

| 2,809,406 | A | 10/1957 | Walter |
| 6,146,588 | A | 11/2000 | Deighton |
| 6,651,288 | B1 | 11/2003 | Hackett |
| 8,871,029 | B1 * | 10/2014 | Leslie ..................... A47L 23/04 134/6 |
| 2004/0078909 | A1 | 4/2004 | Coppa |
| 2011/0262301 | A1 * | 10/2011 | Ghelman .................. A61L 2/07 422/26 |
| 2013/0101461 | A1 * | 4/2013 | Gil ............................ A61L 2/10 422/24 |
| 2013/0174793 | A1 | 7/2013 | Powell |
| 2014/0259482 | A1 | 9/2014 | Bove |

* cited by examiner

*Primary Examiner* — Sean E Conley

(57) ABSTRACT

A surface disinfecting assembly for sterilizing a sole of a shoe includes a box that is positionable on a floor and is positioned adjacent to a selected area such that the box can be stepped in. A pad is positionable in the box and the pad is infused with a fluid antiseptic. In this way the pad sanitize a sole of the shoe thereby inhibiting the shoe from transferring bacteria into the selected area. A cushion is positionable adjacent to the box and the cushion can be stepped upon. The cushion is comprised of a fluid absorbent material for absorbing the fluid antiseptic from the sole of the shoe after the pad is stepped upon.

18 Claims, 7 Drawing Sheets

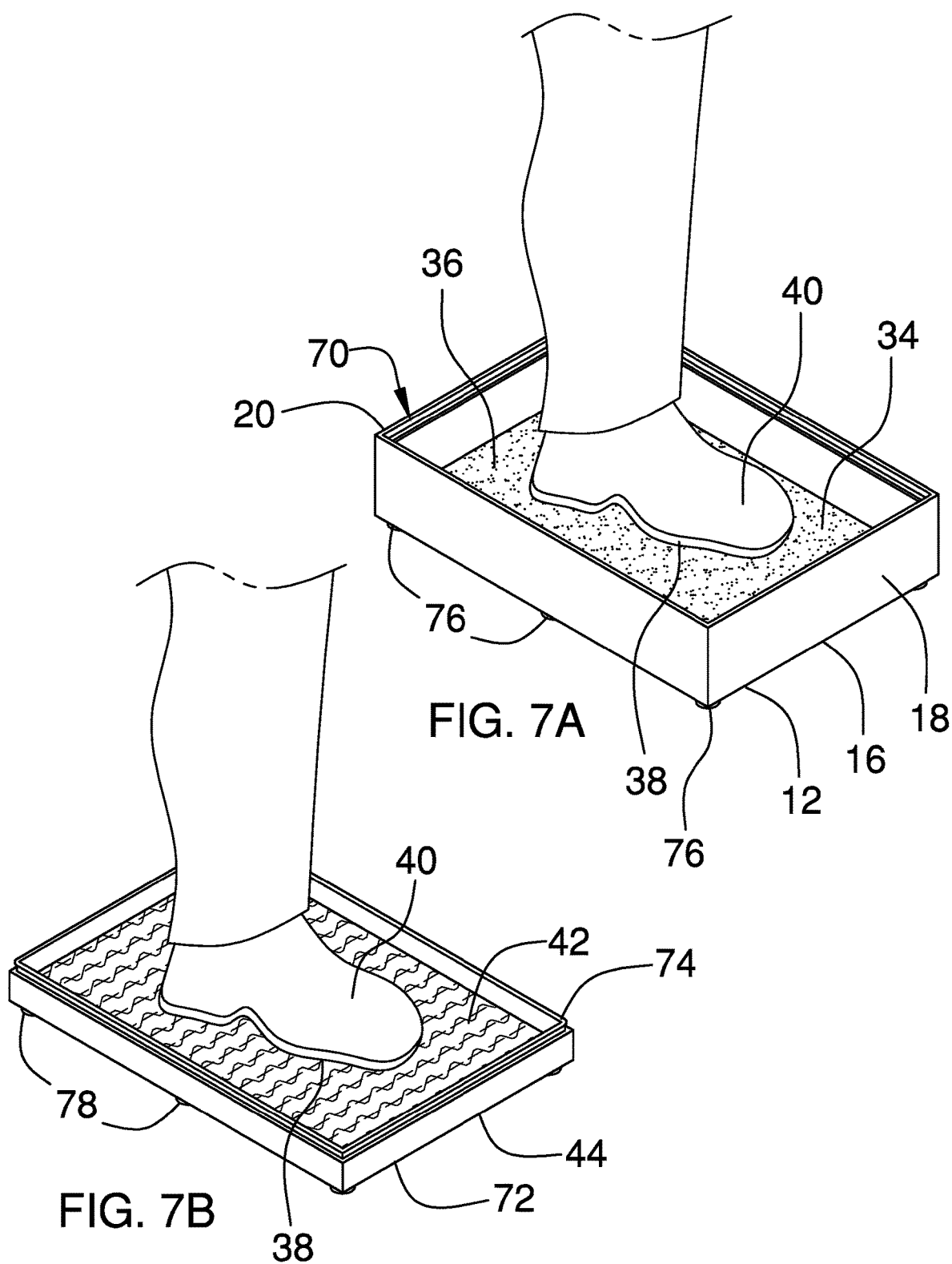

SHOE DISINFECTING ASSEMBLY

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to disinfecting devices and more particularly pertains to a new disinfecting device for disinfecting a sole of a shoe.

BRIEF SUMMARY OF THE INVENTION

An embodiment of the disclosure meets the needs presented above by generally comprising a box that is positionable on a floor and is positioned adjacent to a selected area such that the box can be stepped in. A pad is positionable in the box and the pad is infused with a fluid antiseptic. In this way the pad sanitizes a sole of the shoe thereby inhibiting the shoe from transferring bacteria into the selected area. A cushion is positionable adjacent to the box and the cushion can be stepped upon. The cushion is comprised of a fluid absorbent material for absorbing the fluid antiseptic from the sole of the shoe after the pad is stepped upon.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 7A is a perspective in-use view of an alternative embodiment of the disclosure.

FIG. 7B is a perspective in use view of an alternative embodiment of the disclosure.

DETAILED DESCRIPTION OF THE INVENTION

Figure 1:
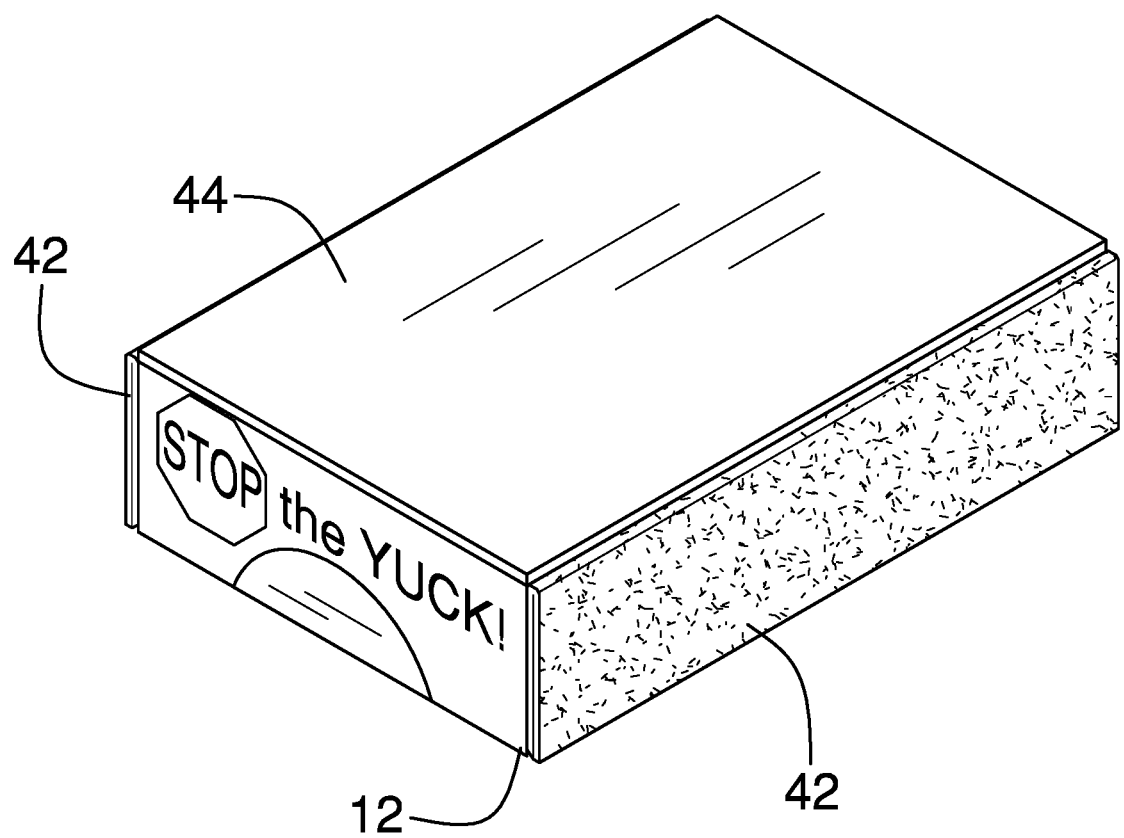
FIG. 1 is a perspective view of a surface disinfecting assembly according to an embodiment of the disclosure.
Figure 2:
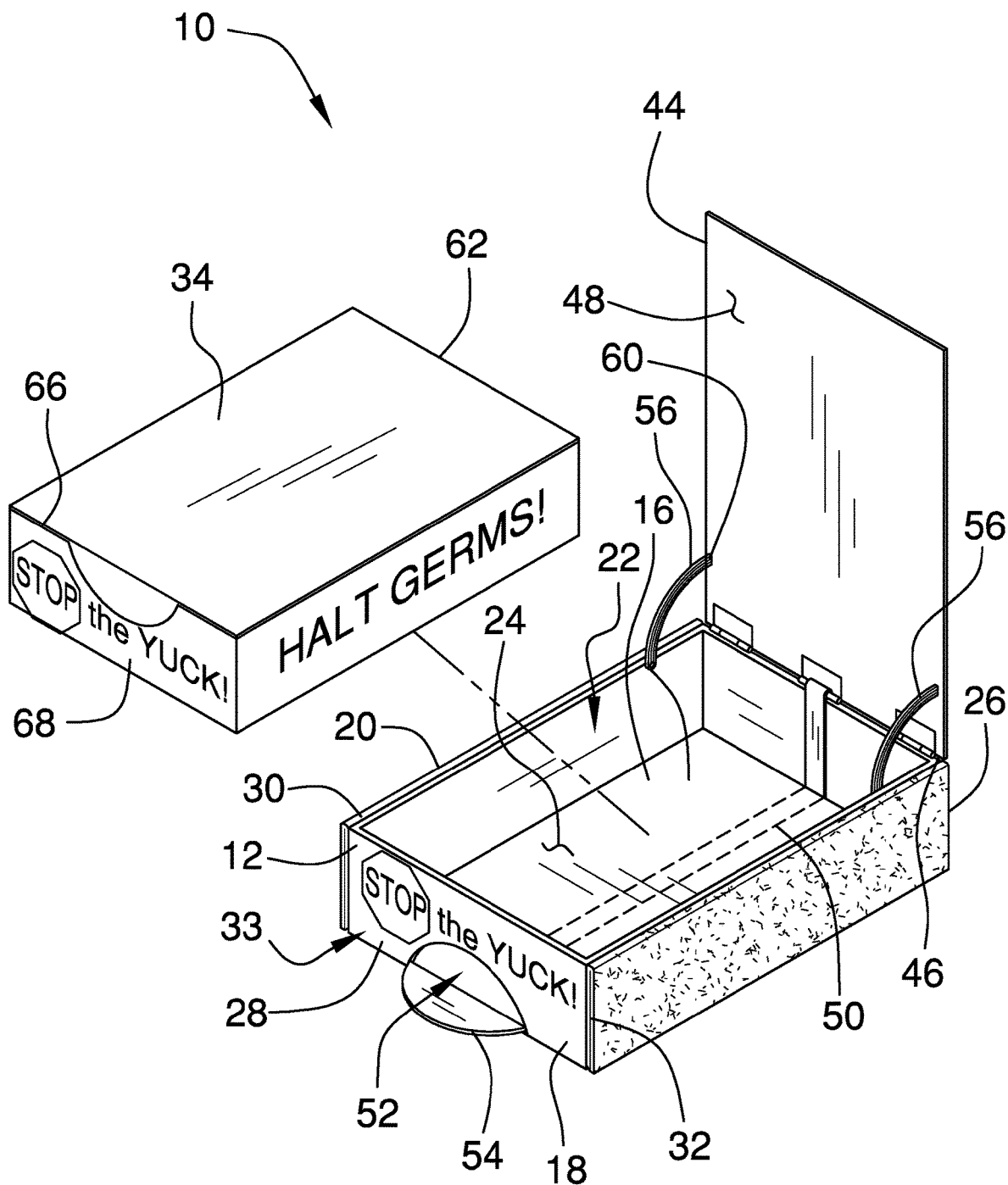
FIG. 2 is an exploded view of an embodiment of the disclosure.
Figure 3:
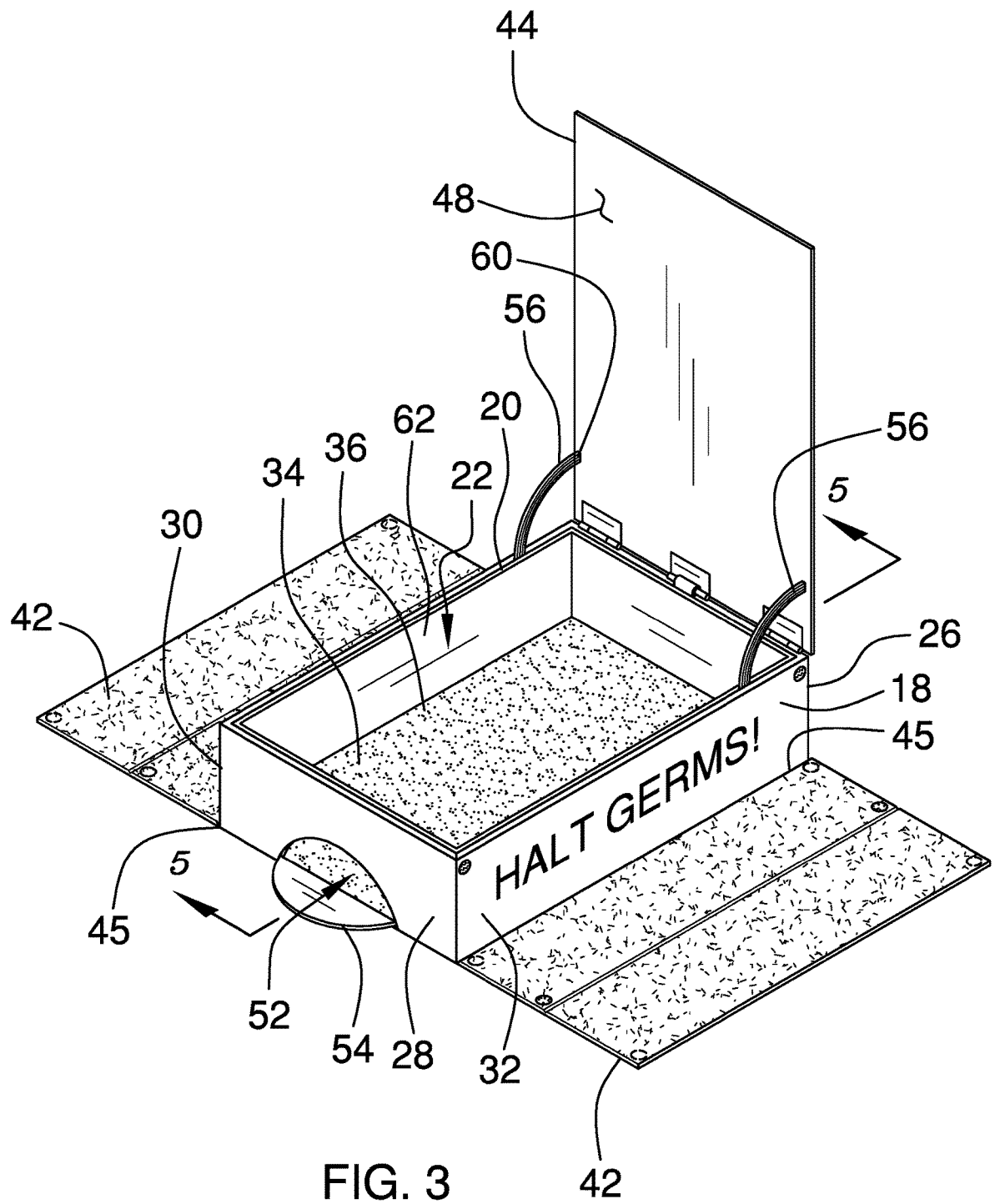
FIG. 3 is a perspective view of an embodiment of the disclosure showing a pair of cushions in a deployed position.
Figure 4:
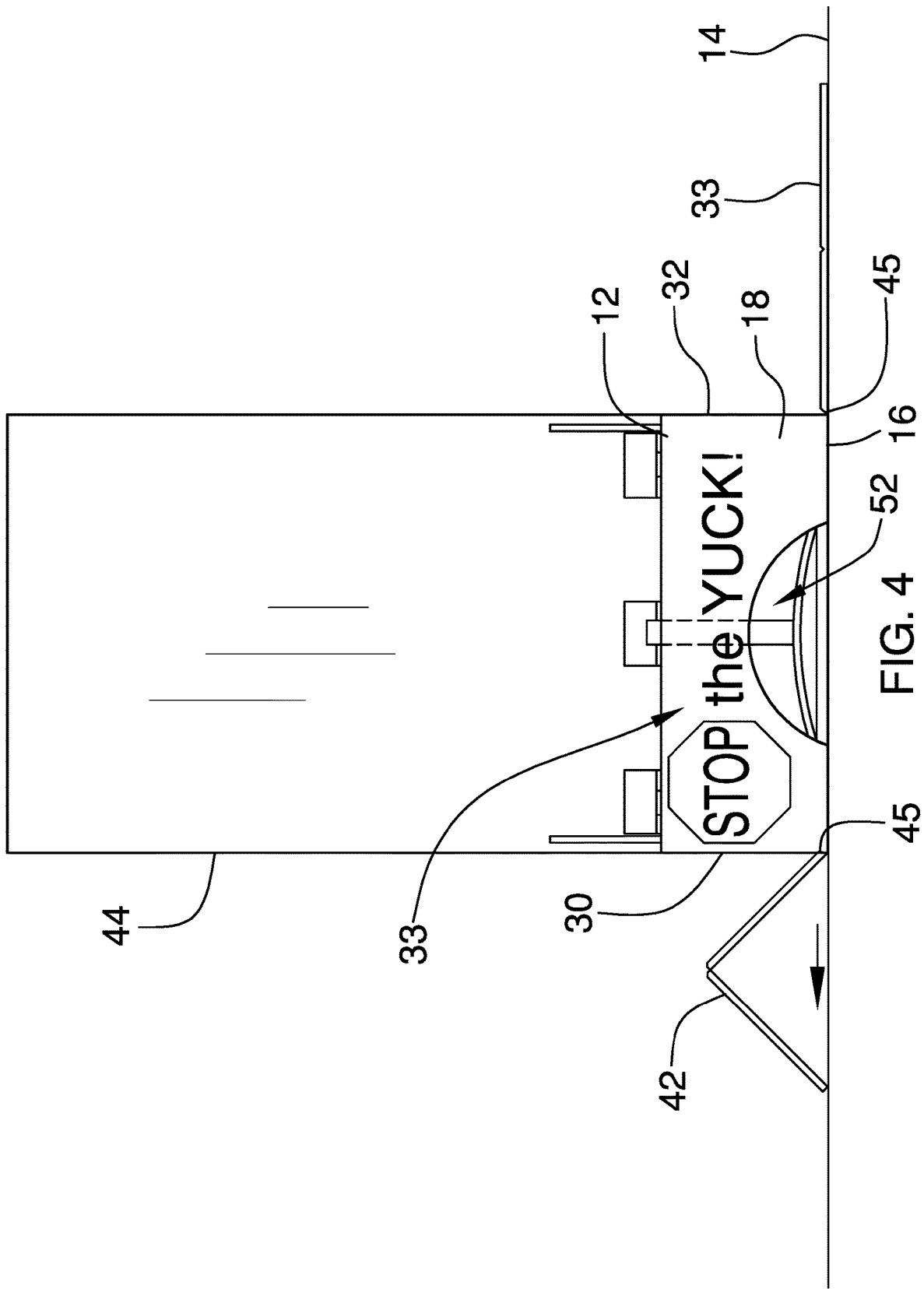
FIG. 4 is a front view of an embodiment of the disclosure.
Figure 5:
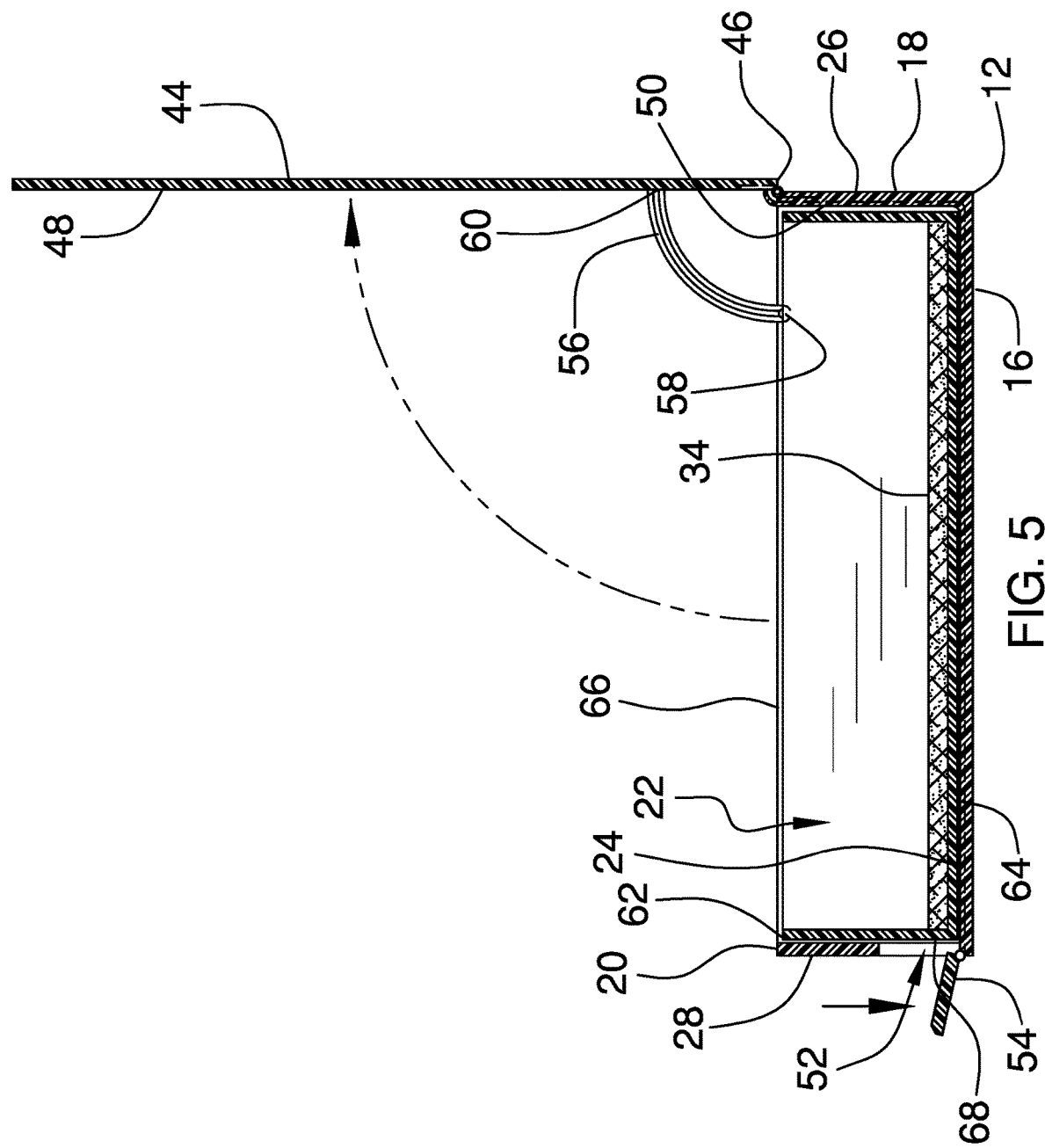
FIG. 5 is a cross sectional view taken along line 5-5 of FIG. 3 of an embodiment of the disclosure.

With reference now to the drawings, and in particular to FIGS. 1 through 7 thereof, a new disinfecting device embodying the principles and concepts of an embodiment of the disclosure and generally designated by the reference numeral 10 will be described.

As best illustrated in FIGS. 1 through 7B, the surface disinfecting assembly 10 generally comprises a box 12 that is positionable on a floor 14 and is positioned adjacent to a selected area. Moreover, the box 12 is stepped in when a user walks on the floor 14 and enters the selected area. The floor 14 may be a floor 14 in a building and the selected area may be a room in the building. The box 12 has a bottom wall 16 and an outer wall 18 extending upwardly therefrom, and the outer wall 18 has a distal edge 20 with respect to the bottom wall 16 defining an opening 22 into the box 12. The bottom wall 16 has a top surface 24 and the outer wall 18 has a back side 26, a front side 28, a first lateral side 30 and a second lateral side 32. Indicia 33 may be printed on the front side 28 and the indicia 33 may comprise a Stop sign followed by the words "the YUCK!". The Indicia 33 may further include the words "Halt Germs" on the first 30 and second 32 lateral sides.

A pad 34 is provided and the pad 34 is positionable in the box 12 thereby facilitating the pad 34 to be stepped upon. Moreover, the pad 34 is infused with a fluid antiseptic 36 to sanitize a sole 38 of a shoe 40 thereby inhibiting the shoe 40 from transferring bacteria into the selected area. The fluid antiseptic 36 may be a liquid antiseptic of any conventional design and chemistry. A cushion 42 is provided and the cushion 42 is positionable adjacent to the box 12 thereby facilitating the cushion 42 to be stepped upon. The cushion 42 is comprised of a fluid absorbent material for absorbing the fluid antiseptic 36 from the sole 38 of the shoe 40 after the pad 34 is stepped upon. A lid 44 is provided and the lid 44 is positionable in a closed position for closing the box 12.

As shown in FIGS. 1 through 5, a pair of the cushions 42 is provided and each of the cushions 42 has a first edge 45. The first edge 45 of each of the cushions 42 is coupled to a respective one of the first 30 and second 32 lateral sides of the outer wall 18 of the box 12. Each of the cushions 42 is foldable into a stored position having each of the cushions 42 lying against the respective first 30 and second 32 lateral sides. Alternatively, each of the cushions 42 is unfoldable into a deployed position has each of the cushions 42 lying on the floor 14 and extending laterally away from the respective first 30 and second 32 lateral sides.

As shown in FIGS. 1 through 5, the lid 44 has a back edge 46 and a bottom surface 48, and the back edge 46 is hingedly coupled to the distal edge 20 of the outer wall 18 of the box 12 corresponding to the back side 26 of the outer wall 18. The bottom surface 48 of the lid 44 rests on the distal edge 20 of the outer wall 18 when the lid 44 is positioned in a closed position. Additionally, the lid 44 extends upwardly from the back side 26 of the outer wall 18 when the lid 44 is positioned in an open position.

As shown in FIGS. 1 through 5, a lifting mechanism 50 is slidably coupled to the box 12. The lifting mechanism 50 extends between the front side 28 of the outer wall 18 of the box 12 and the back edge 46 of the lid 44. The lifting mechanism 50 may be slidably positioned within the bottom wall 16 of the box 12. The front side 28 of the outer wall 18 of the box 12 may have an aperture 52 extending therethrough and a pedal 54 is pivotally coupled to the front side 28 of the outer wall 18 of the box 12. The pedal 54 is coupled to the lifting mechanism 50 and the pedal 54 may be aligned with the aperture 52 in the box 12 for accommodating toes when the pedal 54 is stepped on. The lifting mechanism 50 urges the lid 44 into the open position when the pedal 54 is stepped on and the lifting mechanism 50 lowers the lid 44 into the closed position when the pedal 54 is not stepped on.

As shown in FIGS. 1 through 4, a pair of braces 56 is provided, each of the braces 56 has a first end 58 and a second end 60, and each of the braces 56 is concavely arcuate between the first 58 and second 60 ends. The first end 58 of each of the braces 56 is slidably coupled to a respective one of the first 30 and second 32 lateral sides of the outer wall 18 of the box 12. The second end 60 of each of the braces 56 is coupled to the bottom surface 48 of the lid 44. A container 62 is provided that has a bottom end 64, a top end 66 and an outside wall 68 extending therebetween, and the top end 66 is open. The plurality of the pads 34 is provided and each of the plurality of pads 34 is stored in the container 62. Additionally, the container 62 can be stored within the box 12 for transportation or for storage.

Figure 6:
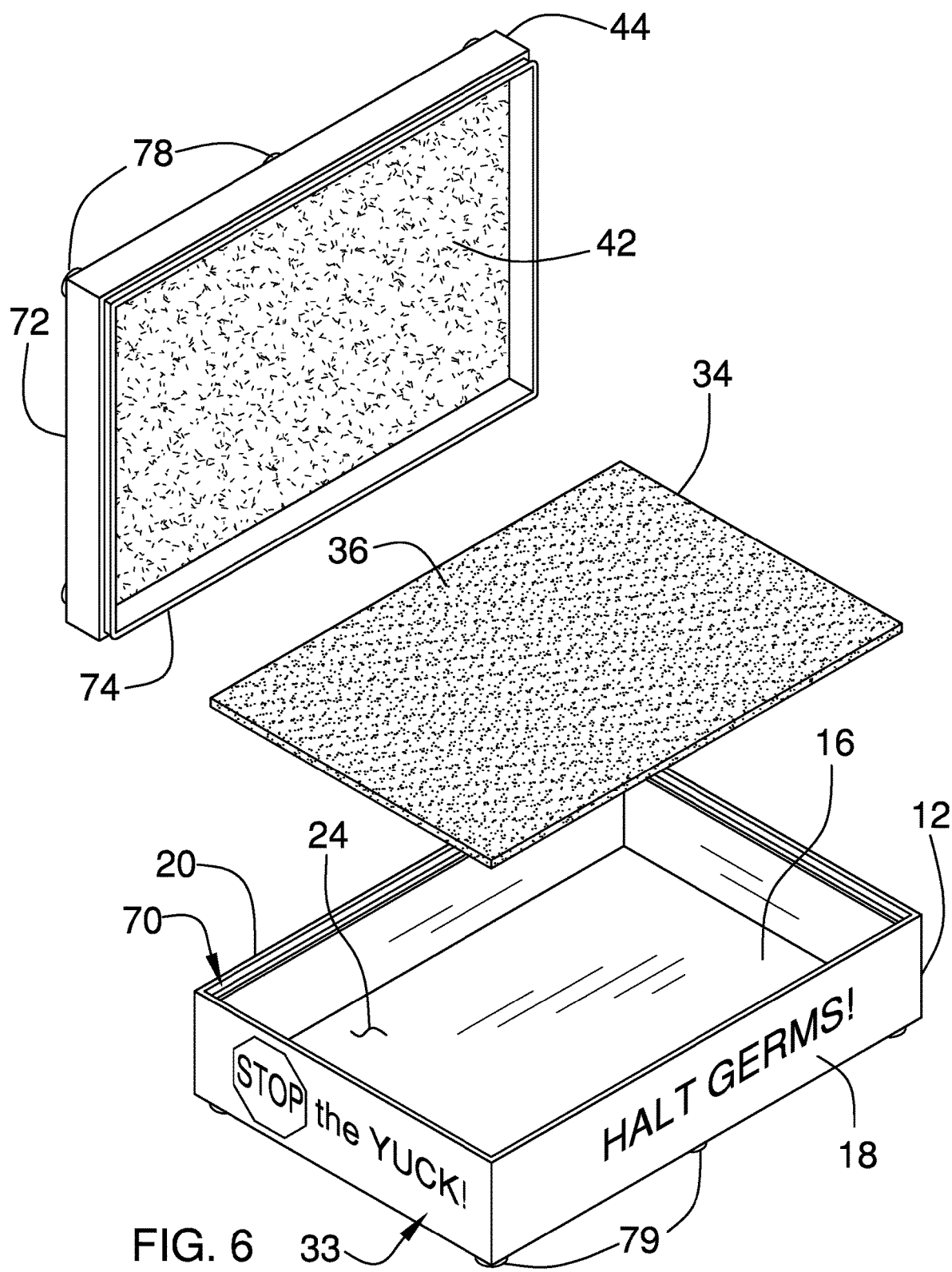
FIG. 6 is a perspective view of an alternative embodiment of the disclosure.

As shown in FIGS. 6 and 7, the distal edge 20 of the outer wall 18 of the box 12 has a groove 70 extending downwardly toward the bottom wall 16 of the box 12 and the groove 70 is coextensive with the distal edge 20. The lid 44 has a top surface 72 and a lip 74 is coupled to and extends downwardly from the bottom surface 48. The lip 74 is coextensive with a perimeter of the lid 44 and the lip 74 frictionally engages the groove 70 when the lid 44 is positioned on the box 12 to retain the lid 44 on the box 12. Moreover, the cushion 42 is positioned on the bottom surface 48 of the lid 44.

As shown in FIGS. 6 and 7, a plurality of box feet 76 is each coupled to and extends downwardly from the bottom wall 16 of the box 12. Each of the box feet 76 is comprised of a resiliently compressible material for frictionally engaging the floor 14. A plurality of lid feet 78 is each coupled to and extends upwardly from the top surface 24 of the lid 44. The lid 44 is positionable on the floor 14 adjacent to the box 12 having each of the lid feet 78 engaging the floor 14 thereby facilitating the lid 44 to be stepped on. In this way the cushion 42 is exposed on the lid 44 for stepping on and absorbing the fluid antiseptic 36 that has been deposited on the sole 38 of the shoe 40.

In use, as shown in FIGS. 1 through 5, the box 12 is positioned on the floor 14 adjacent to the selected area. The container 62 is removed from the box 12 and a selected one of the pads 34 is removed from the container 62 and is positioned in the box 12. Additionally, each of the pair of cushions 42 is unfolded into the deployed position. The pedal 54 is stepped on the open the lid 44 and the pad 34 is stepped upon. Thus, the fluid antiseptic 36 in the pad 34 sterilizes the sole 38 of the shoe 40. The cushions 42 are stepped upon the dry the sole 38 of the shoe 40 when the sole 38 of the shoe 40 has been sterilized. Thus, the shoe 40 is inhibited from transferring bacteria into the selected area.

As shown in FIGS. 6 through 7A and 7B, the box 12 is positioned on the floor 14 adjacent to the selected area. The lid 44 is removed from the box 12 and the lid 44 is positioned next to the box 12. The pad 34 is positioned in the box 12 thereby facilitating the pad 34 to be stepped upon for sterilizing the sole 38 of the shoe 40. The cushion 42 in the lid 44 is stepped upon the dry the sole 38 of the shoe 40 when the sole 38 has been sterilized. In this way the shoe 40 is inhibited from transferring bacteria into the selected area.

While described above generally as a surface disinfecting assembly 10 and more specifically providing for the surface to be a shoe, it is intended and should be understood that the assembly 10 may be used equally to disinfect ambulatory aides including but not limited to canes, walkers, crutches, and the like. Further, the box 12 may be sized to allow for two legs of a walker to be inserted into the box simultaneously wherein a walker having four legs total would only have to be manipulated to place legs into the box twice.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A surface disinfecting assembly being configured to sanitize a sole on a shoe thereby inhibiting the shoe from transferring bacteria into a selected area, said assembly comprising:

a box being positionable on a floor and being positioned adjacent to a selected area wherein said box is configured to be stepped in, said box having a bottom wall and an outer wall extending upwardly therefrom, said outer wall having a distal edge with respect to said bottom wall defining an opening into said box, said bottom wall having a top surface, said outer wall having a back side, a front side, a first lateral side and a second lateral side;

a pad being positionable in said box wherein said pad is configured to be stepped upon, said pad being infused with a fluid antiseptic wherein said pad is configured to sanitize a sole of the shoe thereby inhibiting the shoe from transferring bacteria into the selected area;

a cushion being positionable adjacent to said box wherein said cushion is configured to be stepped upon, said cushion being comprised of a fluid absorbent material for absorbing the fluid antiseptic from the sole of the shoe after said pad is stepped upon, said cushion being one of a pair of cushions, each of said cushions having a first edge, said first edge of each of said cushions being coupled to a respective one of said first and second lateral sides of said outer wall of said box; and a lid being positionable in a closed position for closing said box.

2. The assembly according to claim 1, wherein each of said cushions is foldable into a stored position having each of said cushions lying against said respective first and second lateral sides, each of said cushions being unfoldable into a deployed position having each of said cushions lying on the floor and extending laterally away from said respective first and second lateral sides.

3. The assembly according to claim 2, wherein said lid has a back edge and a bottom surface, said back edge being hingedly coupled to said distal edge of said outer wall of said box corresponding to said back side of said outer wall, said bottom surface of said lid resting on said distal edge of said outer wall when said lid is positioned in a closed position, said lid extending upwardly from said back side of said outer wall when said lid is positioned in an open position.

4. The assembly according to claim 3, further comprising:
a lifting mechanism being slidably coupled to said box, said sliding mechanism extending between said front side of said outer wall of said box and said back edge of said lid; and
a pedal being pivotally coupled to said front side of said outer wall of said box, said pedal being coupled to said lifting mechanism, said lifting mechanism urging said lid into said open position when said pedal is stepped on, said lifting mechanism lowering said lid into said closed position when said pedal is not stepped on.

5. The assembly according to claim 4, further comprising a pair of braces, each of said braces having a first end and a second end, each of said braces being concavely arcuate between said first and second ends, said first end of each of said braces being slidably coupled to a respective one of said first and second lateral sides of said outer wall of said box, said second end of each of said braces being coupled to said bottom surface of said lid.

6. The assembly according to claim 5, further comprising a container having a bottom end, a top end and an outside wall extending therebetween, said top end being open, said container having said pad being stored therein.

7. The assembly according to claim 1, wherein said distal edge of said outer wall of said box has a groove extending downwardly toward said bottom wall of said box, said groove being coextensive with said distal edge.

8. The assembly according to claim 7, further comprising a plurality of box feet, each of said box feet being coupled to and extending downwardly from said bottom wall of said box, each of said box feet being comprised of a resiliently compressible material for frictionally engaging the floor.

9. A surface disinfecting assembly being configured to sanitize a sole on a shoe thereby inhibiting the shoe from transferring bacteria into a selected area, said assembly comprising:
a box being positionable on a floor and being positioned adjacent to a selected area wherein said box is configured to be stepped in, said box having a bottom wall and an outer wall extending upwardly therefrom, said outer wall having a distal edge with respect to said bottom wall defining an opening into said box, said bottom wall having a top surface, said outer wall having a back side, a front side, a first lateral side and a second lateral side, said distal edge of said outer wall of said box having a groove extending downwardly toward said bottom wall of said box, said groove being coextensive with said distal edge;
a pad being positionable in said box wherein said pad is configured to be stepped upon, said pad being infused with a fluid antiseptic wherein said pad is configured to sanitize a sole of the shoe thereby inhibiting the shoe from transferring bacteria into the selected area;
a cushion being positionable adjacent to said box wherein said cushion is configured to be stepped upon, said cushion being comprised of a fluid absorbent material for absorbing the fluid antiseptic from the sole of the shoe after said pad is stepped upon;
a lid being positionable in a closed position for closing said box, said lid has a bottom surface and a top surface, said lid having a lip being coupled to and extending downwardly from said bottom surface, said lip being coextensive with a perimeter of said lid, said lip frictionally engaging said groove when said lid is positioned on said box to retain said lid on said box, said cushion being positioned on said bottom surface of said lid; and
a plurality of box feet, each of said box feet being coupled to and extending downwardly from said bottom wall of said box, each of said box feet being comprised of a resiliently compressible material for frictionally engaging the floor.

10. The assembly according to claim 9, further comprising a plurality of lid feet, each of said lid feet being coupled to and extending upwardly from said top surface of said lid, said lid being positionable on the floor adjacent to said box having each of said lid feet engaging the floor wherein said cushion is exposed for being stepped on.

11. A surface disinfecting assembly being configured to sanitize a sole on a shoe thereby inhibiting the shoe from transferring bacteria into a selected area, said assembly comprising:
a box being positionable on a floor and being positioned adjacent to a selected area wherein said box is configured to be stepped in, said box having a bottom wall and an outer wall extending upwardly therefrom, said outer wall having a distal edge with respect to said bottom wall defining an opening into said box, said bottom wall having a top surface, said outer wall having a back side, a front side, a first lateral side and a second lateral side;
a pad being positionable in said box wherein said pad is configured to be stepped upon, said pad being infused with a fluid antiseptic wherein said pad is configured to sanitize a sole of the shoe thereby inhibiting the shoe from transferring bacteria into the selected area;
a cushion being positionable adjacent to said box wherein said cushion is configured to be stepped upon, said cushion being comprised of a fluid absorbent material for absorbing the fluid antiseptic from the sole of the shoe after said pad is stepped upon;

a lid being positionable in a closed position for closing said box; and said cushion being one of a pair of cushions, each of said cushions having a first edge, said first edge of each of said cushions being coupled to a respective one of said first and second lateral sides of said outer wall of said box, each of said cushions being foldable into a stored position having each of said cushions lying against said respective first and second lateral sides, each of said cushions being unfoldable into a deployed position having each of said cushions lying on the floor and extending laterally away from said respective first and second lateral sides.

12. The assembly according to claim 11, wherein said lid has a back edge and a bottom surface, said back edge being hingedly coupled to said distal edge of said outer wall of said box corresponding to said back side of said outer wall, said bottom surface of said lid resting on said distal edge of said outer wall when said lid is positioned in a closed position, said lid extending upwardly from said back side of said outer wall when said lid is positioned in an open position.

13. The assembly according to claim 12, further comprising:

a lifting mechanism being slidably coupled to said box, said sliding mechanism extending between said front side of said outer wall of said box and said back edge of said lid; and a pedal being pivotally coupled to said front side of said outer wall of said box, said pedal being coupled to said lifting mechanism, said lifting mechanism urging said lid into said open position when said pedal is stepped on, said lifting mechanism lowering said lid into said closed position when said pedal is not stepped on.

14. The assembly according to claim 13, further comprising a pair of braces, each of said braces having a first end and a second end, each of said braces being concavely arcuate between said first and second ends, said first end of each of said braces being slidably coupled to a respective one of said first and second lateral sides of said outer wall of said box, said second end of each of said braces being coupled to said bottom surface of said lid.

15. The assembly according to claim 14, further comprising a container having a bottom end, a top end and an outside wall extending therebetween, said top end being open, said container having said pad being stored therein.

16. A surface disinfecting assembly being configured to sanitize a sole on a shoe thereby inhibiting the shoe from transferring bacteria into a selected area, said assembly comprising:

a box being positionable on a floor and being positioned adjacent to a selected area wherein said box is configured to be stepped in, said box having a bottom wall and an outer wall extending upwardly therefrom, said outer wall having a distal edge with respect to said bottom wall defining an opening into said box;

a pad being positionable in said box wherein said pad is configured to be stepped upon, said pad being infused with a fluid antiseptic wherein said pad is configured to sanitize a sole of the shoe thereby inhibiting the shoe from transferring bacteria into the selected area;

a cushion being positionable adjacent to said box wherein said cushion is configured to be stepped upon, said cushion being comprised of a fluid absorbent material for absorbing the fluid antiseptic from the sole of the shoe after said pad is stepped upon; and a lid being positionable in a closed position for closing said box;

said distal edge of said outer wall of said box having a groove extending downwardly toward said bottom wall of said box, said groove being coextensive with said distal edge;

said lid having a bottom surface and a top surface, said lid having a lip being coupled to and extending downwardly from said bottom surface, said lip being coextensive with a perimeter of said lid, said lip frictionally engaging said groove when said lid is positioned on said box to retain said lid on said box; and said cushion being positioned on said bottom surface of said lid.

17. The assembly according to claim 16, further comprising a plurality of box feet, each of said box feet being coupled to and extending downwardly from said bottom wall of said box, each of said box feet being comprised of a resiliently compressible material for frictionally engaging the floor.

18. The assembly according to claim 17, further comprising a plurality of lid feet, each of said lid feet being coupled to and extending upwardly from said top surface of said lid, said lid being positionable on the floor adjacent to said box having each of said lid feet engaging the floor wherein said cushion is exposed for being stepped on.

* * * * *